US 8,596,788 B2

(12) United States Patent
Ranchod

(10) Patent No.: US 8,596,788 B2
(45) Date of Patent: Dec. 3, 2013

(54) MULTIPLE-VIEW COMPOSITE OPHTHALMIC IRIDOCORNEAL ANGLE IMAGING SYSTEM

(75) Inventor: Tushar Mahendra Ranchod, Oakland, CA (US)

(73) Assignee: Broadspot Imaging Corporation, Oakland, CA (US)

( * ) Notice: Subject to any disclaimer, the term of this patent is extended or adjusted under 35 U.S.C. 154(b) by 34 days.

(21) Appl. No.: 13/534,604

(22) Filed: Jun. 27, 2012

(65) Prior Publication Data
US 2013/0271729 A1 Oct. 17, 2013

Related U.S. Application Data

(60) Provisional application No. 61/501,705, filed on Jun. 27, 2011.

(51) Int. Cl.
*A61B 3/00* (2006.01)
*A61B 3/125* (2006.01)
*A61B 3/117* (2006.01)

(52) U.S. Cl.
CPC ............... *A61B 3/125* (2013.01); *A61B 3/117* (2013.01)
USPC ............................ 351/219; 351/210; 351/221

(58) Field of Classification Search
CPC ............................... A61B 3/125; A61B 3/117
USPC .......... 351/210, 212, 219, 221, 247; 606/4, 6
See application file for complete search history.

(56) References Cited

U.S. PATENT DOCUMENTS

| 2001/0033362 | A1 | 10/2001 | Sarver | |
| 2004/0196434 | A1* | 10/2004 | Khaw et al. | 351/219 |
| 2010/0128221 | A1 | 5/2010 | Muller et al. | |
| 2010/0134759 | A1* | 6/2010 | Silvestrini et al. | 351/206 |
| 2012/0127430 | A1 | 5/2012 | Rotenstreich et al. | |

OTHER PUBLICATIONS

International Search Report, mailed Sep. 13, 2013, for related International application PCT/US2013/04330, 5 pages.
Written Opinion of the International Searching Authority, mailed Sep. 13, 2013, for related International application PCT/US2013/043302, 5 pages.
Paques, Michael et al., "Panretinal, High-Resolution Color Photography of the Mouse Fundus", Investigative Ophthalmology & Visual Science, Jun. 2007, vol. 48, No. 6, U.S.A., pp. 2769-2774.

* cited by examiner

*Primary Examiner* — Huy K Mai
(74) *Attorney, Agent, or Firm* — Edward J. Radlo; Radlo IP Law Group

(57) ABSTRACT

A device (20) and methods for concurrently taking multiple partially overlapping still or video images (60) of the iridocorneal angle (12) of an eye (1). Device (20) typically comprises a single chassis (100) with an outer surface (101) that approximately matches the curvature of the ocular surface (4). Multiple discrete optical imaging systems (200) are aimed through the cornea (3) and the anterior chamber (17), producing non-coplanar optical paths (21) directed towards corresponding partially overlapping zones (11) of the iridocorneal angle (12). Each system (200) may comprise one or more optical lenses (210, 211), with either fixed or variable position, and a corresponding digital sensor (220) or portion of a larger common shared digital sensor (221).

20 Claims, 5 Drawing Sheets

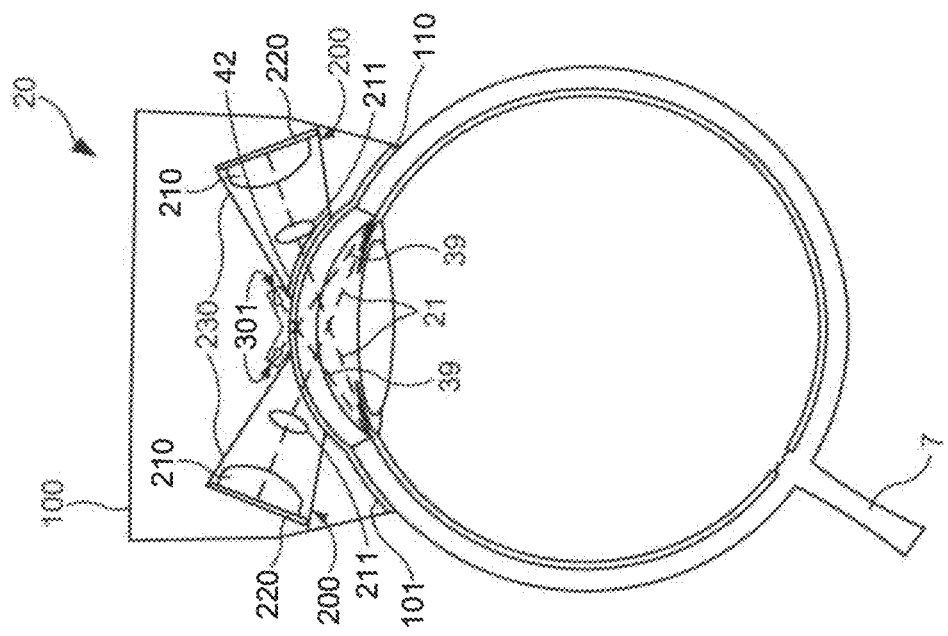
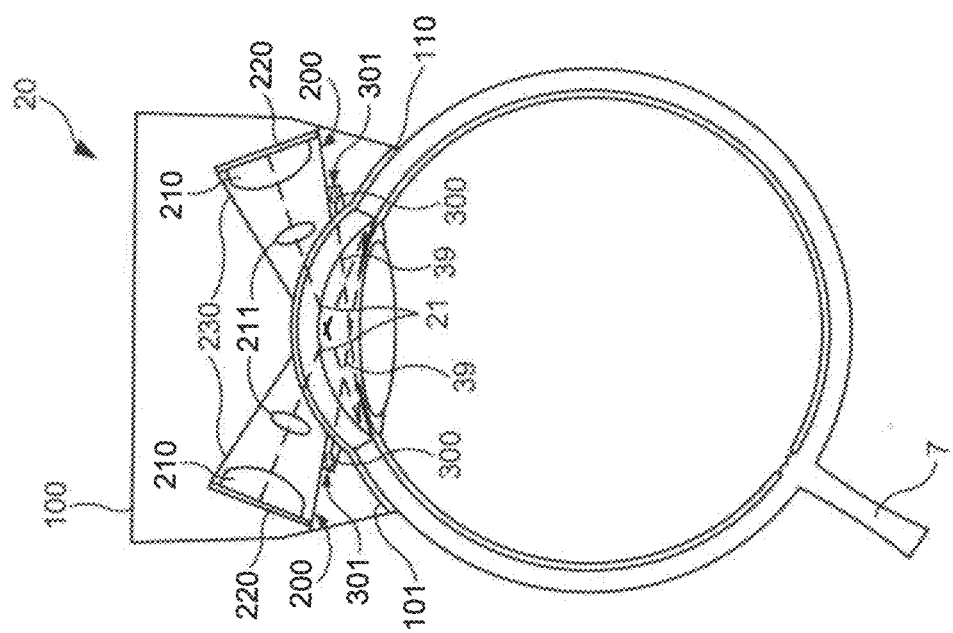

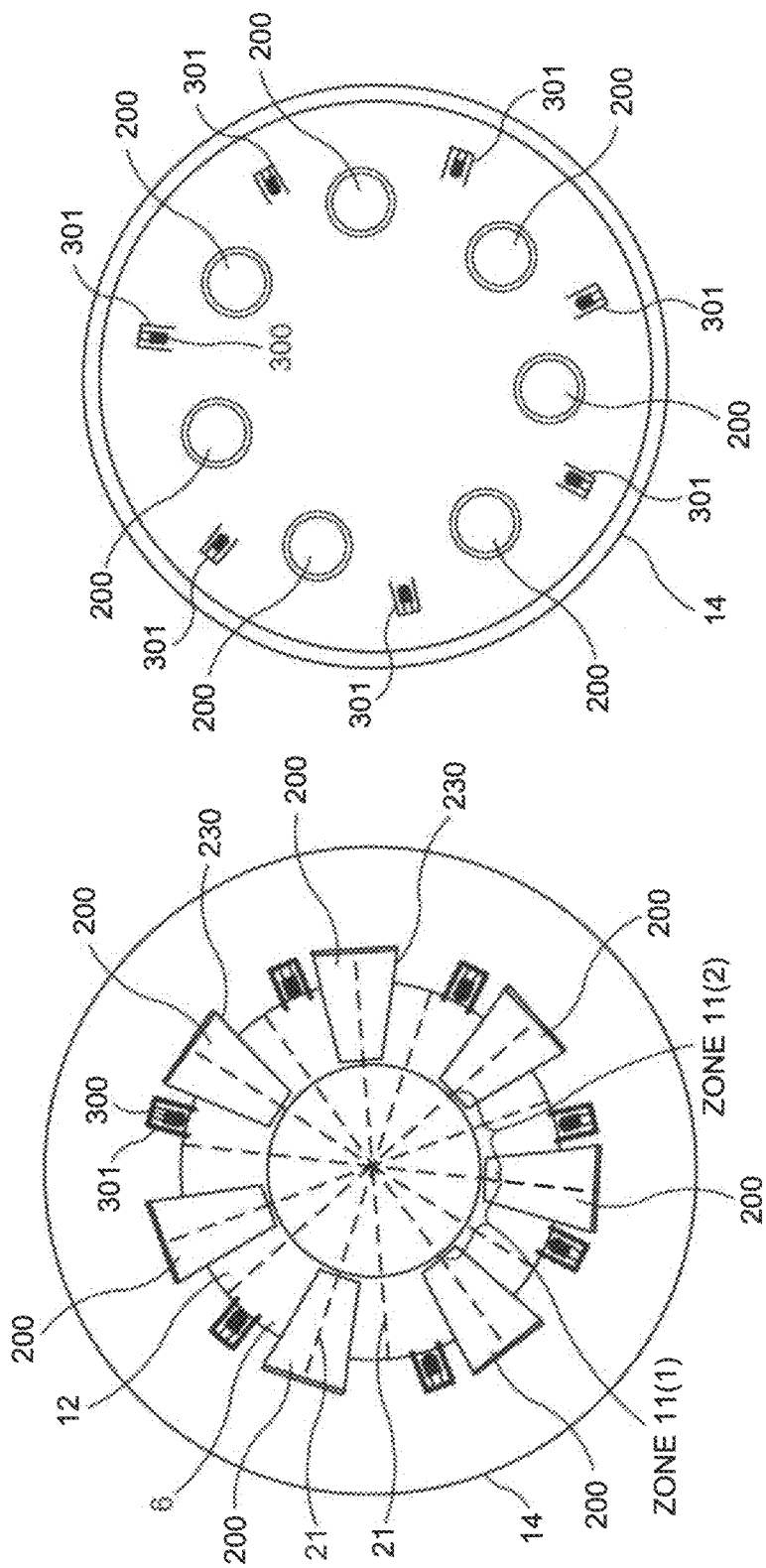

MULTIPLE-VIEW COMPOSITE OPHTHALMIC IRIDOCORNEAL ANGLE IMAGING SYSTEM

RELATED APPLICATIONS

This patent application claims the benefit of commonly owned U.S. provisional patent application Ser. No. 61/501,705 filed Jun. 27, 2011, entitled "Multiple-lens Composite Ophthalmic Iridocorneal Angle Imaging System", which provisional patent application is hereby incorporated by reference in its entirety into the present patent application; and furthermore, commonly owned U.S. patent application Ser. No. 13/485,206 filed May 31, 2012 and entitled "Multiple-Lens Retinal Imaging Device and Methods for Using Device to Identify, Document, and Diagnose Eye Disease", is also incorporated by reference in its entirety into the present patent application.

TECHNICAL FIELD

The present invention relates to an ocular imaging device, particularly one that views the anterior segment of the human eye.

BACKGROUND ART

Ocular imaging is commonly used both to screen for diseases and to document findings discovered during clinical examination of the eye 1. The most common type of photographic ocular imaging is digital photographic imaging of the retina 10. However, imaging of the anterior segment 15 of the human eye 1 is increasingly common, to document pathology of the anterior segment 15, particularly in conjunction with documentation in electronic medical records. Current photographic imaging of the anterior segment 15 is performed primarily using non-contact digital photography. Anterior segment 15 photography has also been performed using contact imaging systems such as the RetCam by Clarity Medical, which was designed primarily for retinal imaging, but which may be used for anterior segment 15 photography as well.

Anterior segment 15 photography may be used to image various ocular structures, including but not limited to: the iridocorneal angle 12; the iris 6; the anterior chamber 17; the crystalline lens 5 or an artificial lens implant; and the anterior vitreous 18.

Documentation of the iridocorneal angle 12 is particularly important in patients diagnosed with glaucoma; patients who are labeled as glaucoma suspects; patients with proliferative ischemic retinal diseases, such as proliferative diabetic retinopathy or central retinal vein occlusion; and patients with blunt traumatic injury to the eye 1. Abnormalities of the iridocorneal angle 12 require imaging with a gonioscopic optical system, since the angle 12 is obscured from direct view on clinical examination by total internal reflection of the cornea 3. Gonioscopic examination or imaging is defined as examination or imaging of the iridocorneal angle 12. In clinical practice, the iridocorneal angle 12 is most commonly visualized using a contact lens with multiple mirrors or prisms; the mirrors or prisms are positioned to avoid total internal reflection while providing views of the angle 12. In small children, ophthalmologists sometimes use a Koeppe direct gonioscopic lens, which allows for visualization of the angle 12 without the assistance of mirrors or prisms.

During clinical examination of the iridocorneal angle 12 with a gonioscopic lens, indentation gonioscopy may be performed. Indentation gonioscopy is a technique of examining the iridocorneal angle 12 while gently applying and releasing pressure against the cornea 3 using the gonioscopic lens. The pressure against the cornea 3 causes an elevation of the intraocular pressure, which consequently changes the anatomic configuration of the iridocorneal angle 12. Indentation gonioscopy is therefore a dynamic examination, which is best captured by digital video rather than still digital images, but which may be captured by still images under varying degrees of pressure.

DISCLOSURE OF INVENTION

The invention described herein represents a significant improvement in photographic examination and documentation of the iridocorneal angle 12. The invention produces an array of partially overlapping images 60 of the iridocorneal angle 12 taken simultaneously from different imaging angles. A single composite digital image 61 can be fabricated by merging the overlapping fields of multiple concurrently captured images 60.

Illumination of the angle 12 can be integrated into the imaging to provide broad illumination of the angle 12 while minimizing light directed at the retina 10. The intensity of illumination may be varied in order to stimulate more or less pupillary constriction, which may also alter the anatomic configuration of the iridocorneal angle 12.

As used herein, "image" means a still image (i.e., photograph) or a moving image (i.e., video).

The invention may be used by eye care providers, such as ophthalmologists or optometrists, in order to document findings seen during clinical examination. The invention may also be used by non-eye care providers in order to capture images 60 of the anterior segment 15 and transmit those images 60 for remote reading by an eye care professional at the same or another facility. The invention may therefore be used for local ophthalmic care or remote care using a telemedicine infrastructure. While retinal imaging in adult patients may be limited in quality by cataract media opacification, anterior segment 15 imaging is rarely limited by media opacities, age-related or otherwise.

BRIEF DESCRIPTION OF THE DRAWINGS

These and other more detailed and specific objects and features of the present invention are more fully disclosed in the following specification, reference being had to the accompanying drawings. The various features of the drawings are not to scale. In some cases, the dimensions of the various features have been arbitrarily expanded or reduced for clarity.

FIG. 2 is a transverse cross-sectional view of an exemplary embodiment of the present invention, in which a single chassis 100 is placed against the ocular surface 4.

FIG. 3 is a view of the FIG. 2 embodiment in which the illumination assemblies 301 are differently placed.

FIG. 6 is a top view showing seven imaging systems 200 and seven illumination sources 300 arranged circumferentially against the cornea 3 to illuminate and capture seven images 60 of seven different overlapping zones 11 of the iridocorneal angle 12.

FIG. 7 is a bottom view of the FIG. 6 embodiment.

DETAILED DESCRIPTION OF PREFERRED EMBODIMENTS

Figure 1:
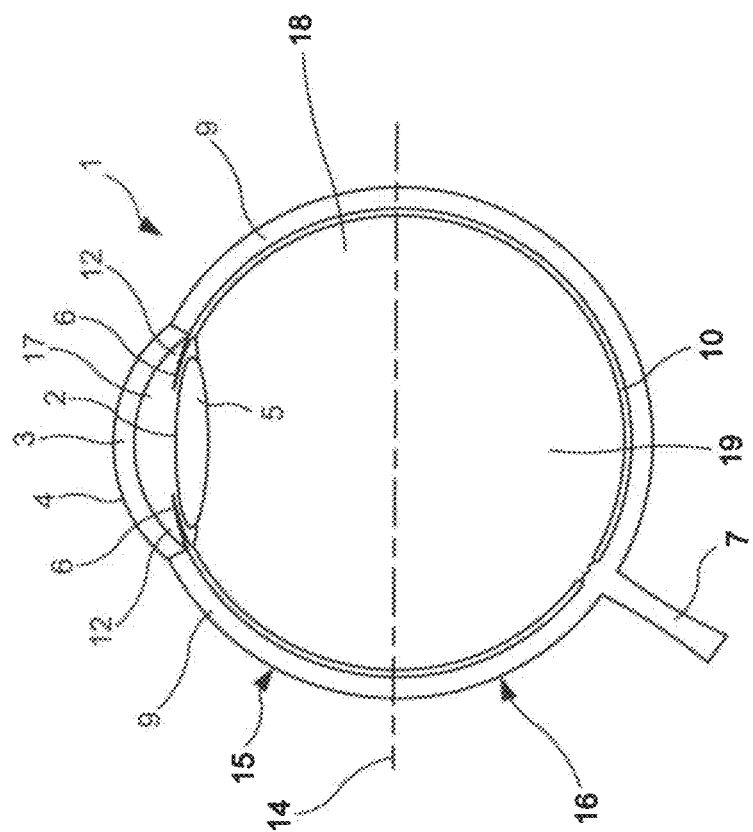
FIG. 1 is a simplified illustration of basic anatomy of the human eye 1 in transverse cross section.

The present invention 20 enables the capture of images 60 of structures in the anterior segment 15 of the eye 1, including the iridocorneal angle 12 and iris 6. The present invention 20 allows for still or video imaging of abnormalities relevant to diseases such as glaucoma, traumatic angle recession, iris 6 tumors, and iris 6 neovascularization.

As shown in FIG. 1, the anterior segment 15 of the eye 1 includes the cornea 3, sclera 9, iridocorneal angle 12, anterior chamber 17, iris 6, lens 5, and anterior vitreous 18, i.e., everything above equator 14 in FIG. 1. The cornea 3 and adjacent sclera 9 constitute the ocular surface 4.

The average corneal diameter in a newborn human is approximately 9-10 mm and in an adult human is approximately 12 mm, but may be lesser or greater in any given individual. The internal optics of the human eye 1 relevant for imaging the iridocorneal angle 12 are determined primarily by the curvature of the cornea 3 and lens 5, the anterior-to-posterior depth of the anterior chamber 17, and the refractive indices of the cornea 3 and aqueous humor.

This invention 20 permits imaging of anterior segment 15 structures, potentially in combination with imaging of the retina 10 (e.g., when used in conjunction with the teachings of the aforesaid U.S. patent application Ser. No. 13/485,206). This allows for iris 6 or iridocorneal angle 12 angiography, or for dynamic video imaging of the entire iridocorneal angle 12, with or without utilizing the technique of indentation gonioscopy.

The invention 20 provides for taking multiple digital photographs 60 or digital video 60 of the iridocorneal angle 12 concurrently and at different angles across the anterior chamber 17 of the eye 1, with or without the use of stereo photographic pairs.

As shown in FIGS. 2 through 5, The inventive device 20 preferably comprises a single chassis 100 with a smooth concave outer (lower) surface 101 that fits against the ocular surface 4, with or without a viscous coupling agent and with or without a disposable or reusable transparent cover 110 positioned between the device 20 and the ocular surface 4. As used herein, "chassis 100" refers to any suitable structure that is able to hold the constituent items (200, 300, 220, 221, 230, etc.) in the desired configuration with respect to the ocular surface 4. The chassis 100 depicted in FIGS. 2 through 5 is a simplified depiction, and does not illustrate the wiring, power source, and attachments which might be necessary for device 20 to function as intended.

Within chassis 100 are multiple discrete optical imaging systems 200. Each system 200 is aimed through the cornea 3 across the anterior chamber 17 towards the iridocorneal angle 12, in order to capture images 60 of different zones 11 of the iridocorneal angle 12. The multiple zones 11 may or may not be partially overlapping. As shown in FIG. 6, they are partially overlapping, which is typical. Each discrete optical imaging system 200 has an optical path 21 aimed through the cornea 3 and across the anterior chamber 17 towards one zone 11 of the iridocorneal angle 12. When viewed from above as in FIG. 6, the discrete optical imaging systems 200 may be arranged in a circular fashion along the corneal midperiphery with approximately radial orientation relative to the center of the cornea 3.

Systems 200 are preferably all non-coplanar with respect to each other. Each system 200 typically uses one or more optical lenses 210, 211 at a fixed angle and either a fixed or variable position, with or without mirrors 235 or prisms, in order to direct an image of one zone 11 of the iridocorneal angle 12 onto a digital sensor 220 that is dedicated to that imaging system 200, or onto part of a common digital sensor 221 that is shared between or among two or more imaging systems 200. In some embodiments, two or more digital sensors 220 may be used for each of one or more of the individual imaging systems 200. The term "digital sensor" as used herein means digital image sensor 220, 221, as well as the accompanying wiring, power supply, hardware, firmware, and/or software needed or desirable for image 60 processing and output.

An imaging system 200 may contain a plurality of lens 210, 211 and/or sensor 220, 221 sub-sections, each of which is used to capture and detect light in a portion of the spectrum. If different light spectra are captured separately at the level of the digital sensors 220, 221, various image 60 types (full color; red-free; angiography-appropriate filtered) can be composed from these separately captured spectra and used for imaging the variety of structures within the eye 1 (some of which may best be observed at specific wavelengths or in the absence of specific wavelengths). Alternatively, if full color images 60 are captured at the level of the sensor 220, 221, various image 60 types can be produced by a combination of hardware, firmware, and/or software after image 60 capture takes place.

Multiple light assemblies 301 are interspersed in between the multiple discrete optical imaging systems 200 within chassis 100. Each light assembly 301 contains one or more illumination sources 300. For example, a light assembly 301 may contain a white light source 300 and a green light source 300, which may be utilized at different times. The intensity of illumination emanating from the light sources 300 may be fixed or variable. An illumination source 300 may be a light emitting diode (LED) or simply the exit point for a distal illumination source of any type that is connected to point 300 by a fiber optic or light pipe. The illumination paths 39 emanating from illumination assemblies 301 are depicted in dashed lines in the Figures.

As used herein, "illumination assembly 301" encompasses the power supply and interconnections necessary to operate the illumination source(s) 300 within assembly 301. Although each illumination source 300 is depicted in FIGS. 2, 3, 6, and 7 as containing one bulb, LED, or other illumination source 300, each source 300 may contain two or more illumination sub-sources having the same or different characteristics (e.g., different intensity or different emitted spectrum of light). Variable intensity of illumination may be desirable, because greater light intensity reduces patient comfort during imaging, and one goal of imaging may be to obtain usable images 60 at the lowest possible illumination intensity. A variable emitted spectrum of light for the illumination sources 300 may be desirable, because certain procedures (such as fluorescein angiography and indocyanine green angiography) require specific light emission spectra from the illumination source 300, in conjunction with image capture filters with different specific light spectra.

Fluorescein angiography is a common type of diagnostic technique used in ophthalmology, in which the eye 1 is illuminated with a 490 nm bandpass filtered blue light, and the sensor 220, 221 captures only 520 nm to 530 nm bandpass filtered yellow-green light. Use of illumination filters can entail device 20 having a second set of illumination sources 300 (one with white light and one with a 490 nm output). Alternatively, one or more systems 200 can have a unique disposable tip 42 (see FIG. 3) that, instead of being clear (for color photography), has colored filters built into it (potentially separate filters for illumination and for imaging). While FIG. 3 shows tip 42 as covering the lower surface of just the rightmost system 200, in some embodiments, tip 42 covers the entire lower surface of chassis 100. Alternatively, the digital sensor(s) 220, 221 can be programmed by software to process only specific wavelengths, or the digital sensor(s) 220, 221 may contain multiple discrete subsensors that process different wavelengths, so filters over the imaging systems 200 may or may not be necessary.

FIG. 3 depicts an embodiment that is identical to the FIG. 2 embodiment, except that the illumination assemblies 301 have been moved from below the optical imaging systems 200 to above the optical imaging systems 200.

Figure 5:
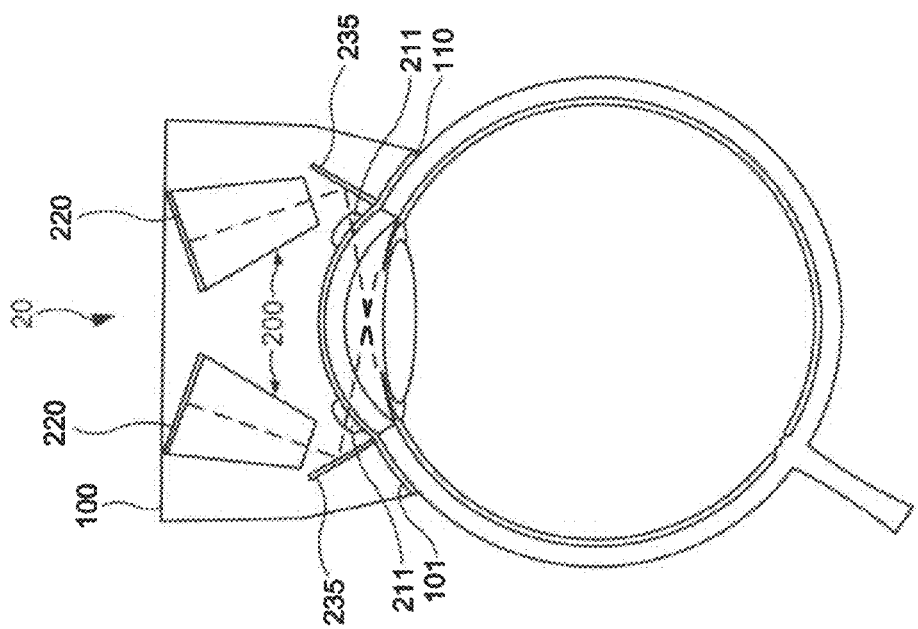
FIG. 5 is a transverse cross-sectional view of an embodiment of the present invention in which mirrors 235 are angled differently than in FIG. 4, and each optical imaging system 200 directs its optical path 21 to a dedicated sensor 220.
Figure 4:
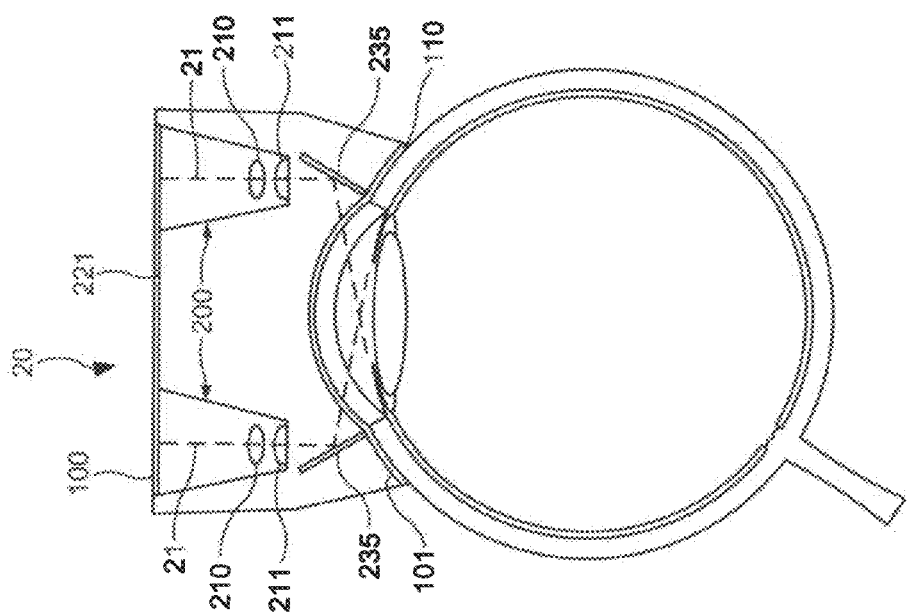
FIG. 4 is a transverse cross-sectional view of an embodiment of the present invention in which multiple optical imaging systems 200 direct their respective optical paths 21 to a single common image sensor 221.

FIGS. 4 and 5 depict the use of mirrors 235 to correct, align, and/or refine the angle of difference between the optical path 21 of any given optical imaging system 200 and the surface(s) of one or more digital sensors 220 or 221. Prisms can be used in lieu of or in addition to mirrors 235.

The multiple partially overlapping digital photographs or videos 60 produced by the sensors 220, 221 and related items (such as hardware, firmware, software, a display, etc.) can be combined to fabricate a single composite photograph or video 61 (FIG. 8) of the iridocorneal angle 12 with a field of view wider than any one of the individual images 60. Exemplary uses of such composite photographs or videos 61 of the iridocorneal angle 12 include but are not limited to color imaging, color imaging with separated or limited channels on the visible color spectrum, red-free imaging, and angiography with intravenous administration of a dye such as fluorescein.

FIG. 6 depicts a top view of eye 1 with multiple discrete optical imaging systems 200 arranged circumferentially around the corneal center, with each optical path 21 directed between an optical imaging system 200 and one zone 11 of the iridocorneal angle 12. Chassis 100 is not shown in FIG. 6, to avoid cluttering the drawing.

FIGS. 6 and 7 illustrate an embodiment of the present invention in which chassis 100 contains seven discrete optical imaging systems 200, as well as seven light assemblies 301. The optical imaging systems 200 are preferably separated from each other by opaque dividers 230, which prevent reflection or transmission of light. Different numbers and distributions of optical imaging systems 200 and light assemblies 301 can be used. Multiple illumination assemblies 301 are shown interspersed among the multiple optical imaging systems 200, with each illumination assembly 301 directed at one zone 11 of the iridocorneal angle 12, but each illumination assembly 301 may be directed across multiple zones 11, or multiple illumination assemblies 301 may be directed at any individual zone 11.

Figure 8:
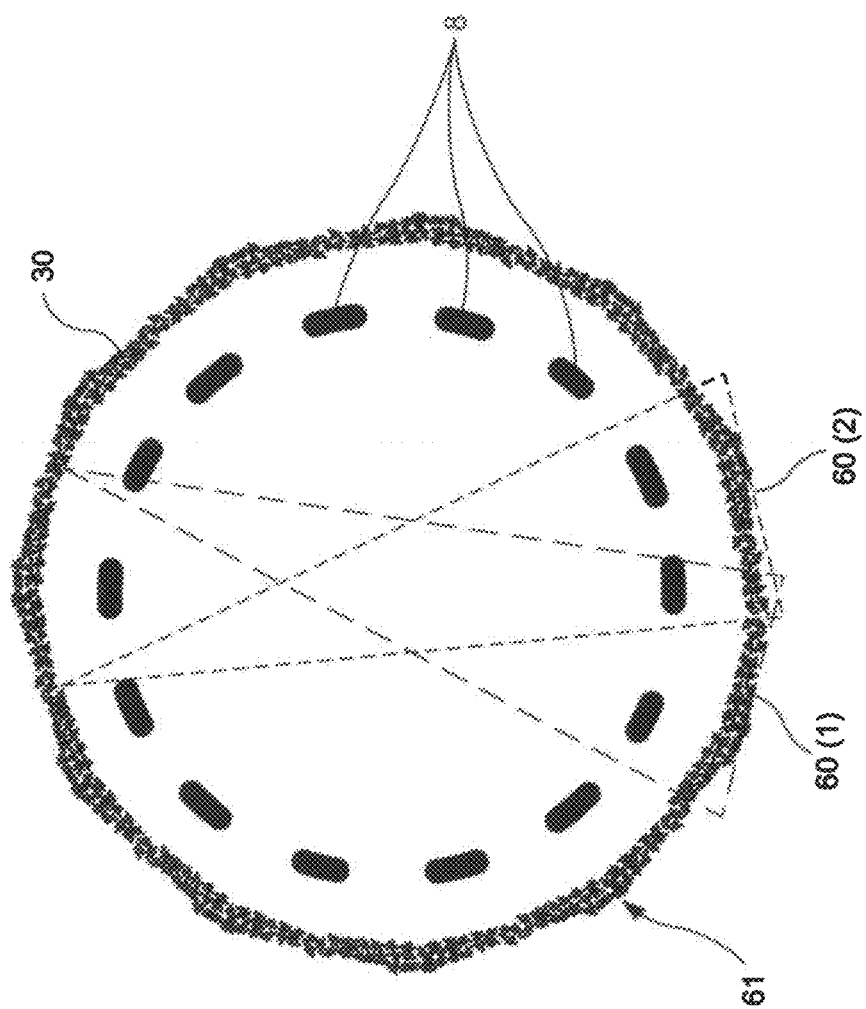
FIG. 8 is a planar view of a composite image 61 fabricated using teachings of the present invention.

FIG. 8 is a representation of multiple partially overlapping images 60 of the iridocorneal angle 12 that have been merged in the overlapping regions to produce a single composite iridocorneal angle image 61 with minimal optical distortion. The individual images 60 shown in FIG. 8 correspond to the individual zones 11 shown in FIG. 6. The outer ring 30 in FIG. 8 is the pigmented trabeculum. The inner dashed ring 8 is the ciliary body.

The merging of multiple images 60 into a single composite image 61 is facilitated by the fixed relative position and known relative focal points of the discrete optical imaging systems 200 used to obtain the photographs or videos 60. The creation of the composite image 61 can be fully automated, and can be produced through any combination of hardware, firmware, and/or software, either immediately following image 60 acquisition or on demand some time following image 60 acquisition. In essence, camera 20 has the capability to take a continuous composite image 61 of the iridocorneal angle 12 and adjacent structures over 360°, with or without stereo pairs.

The relative focal points of the optical imaging systems 200 may be fixed, or may be varied with respect to one another, either on-the fly or according to a predefined algorithm, in order to produce multiple partially overlapping retinal photographs 60 which are all optimally focused and which have minimal optical distortion at their edges.

Focusing may be achieved in one of several ways: 1) moving the lenses 210, 211 by servos; 2) moving the lenses 210, 211 by a manual mechanism (like a traditional camera zoom lens, for example); 3) light field imaging using fish-eye lens arrays and post-hoc software reconstruction (like the Lytro and Pelican cell phones and DSLR cameras, respectively); or 4) configuring chassis 100 (or one or more individual imaging systems 200) to have a long depth of field, with one or more different versions of a disposable tip 42 (see FIG. 3) that fits on the bottom 101 of chassis 100, with a certain focal power associated with that tip 42. For example, one version of the tip 42 can be suitable for a pediatric eye 1 or an eye 1 with a small diameter or shallow anterior chamber 17, a second version of the tip 42 can be suitable for a normal adult eye 1, and a third version of the tip 42 can be suitable for an eye 1 with a large diameter or deep anterior chamber 17.

Tip 42 is typically single use for each patient, and may or may not have optical power that relates to either the illumination or imaging aspects of the imaging system 200. Tip 42 can be clear or contain color filters such as those needed for angiography.

The above description is included to illustrate the operation of preferred embodiments, and is not meant to limit the scope of the invention. The scope of the invention is to be limited only by the following claims.

From the above discussion, many variations will be apparent to one skilled in the art that would yet be encompassed by the spirit and scope of the present invention. For example, this invention can be used to image eyes other than human eyes, such as the eyes of non-human animals.

What is claimed is:

1. A device for imaging the iridocorneal angle of an eye, said device comprising:
 at least two optical imaging systems, each system oriented to image a particular zone of the iridocorneal angle;
 coupled to each system, at least one sensor area for capturing image information corresponding to that system; and
 coupled to the sensor areas, means for generating individual images of zones of the iridocorneal angle corresponding to the systems.

2. The device of claim 1 wherein each image is a still image.

3. The device of claim 1 wherein each image is a video image.

4. The device of claim 1 further comprising, coupled to the generating means, means for fabricating a composite image from the individual images.

5. The device of claim 4 wherein the fabricating means is fully automated.

6. The device of claim 1 wherein no two systems lie in the same plane.

7. The device of claim 1 further comprising a plurality of illumination assemblies interspersed among the systems, wherein each assembly contains one or more illumination sources.

8. The device of claim 7 wherein at least one illumination source is adjustable with respect to at least one of intensity and wavelength.

9. The device of claim 1 wherein at least one system comprises at least one lens.

10. The device of claim 1 wherein the systems are separated by opaque dividers.

11. The device of claim 1 wherein at least two systems share a common sensor.

12. The device of claim 1 wherein at least one system comprises a prism or mirror.

13. The device of claim 1 wherein the systems are contained within a single chassis; and
the chassis is optically coupled to the eye via a disposable or reusable transparent cover.

14. The device of claim 1 further comprising a disposable tip situated between at least one system and the eye, said tip containing a wavelength filter.

15. A method for imaging an iridocorenal angle of an eye, said method comprising the steps of:
simultaneously focusing at least two optical imaging systems onto different zones of the iridocorneal angle;
capturing imaging information corresponding to each system; and
gathering the imaging information from the systems to generate a plurality of individual images, each individual image corresponding to the zone associated with that system.

16. The method of claim 15 wherein the imaging is used to detect at least one of glaucoma, traumatic angle recession, an iris tumor, and an iris neovascularization.

17. The method of claim 15 further comprising the step of combining the individual images together to form a composite image of a wide field of the iridocorneal angle.

18. The method of claim 15 further comprising the step of varying the focal point of at least one system.

19. The method of claim 15 further comprising the step of illuminating the iridocorneal angle simultaneously with the step of capturing the imaging information.

20. The method of claim 19 wherein the illuminating step comprises varying at least one of intensity and wavelength of at least one illumination source.

* * * * *